US012564614B2

(12) United States Patent
Portillo Rosado

(10) Patent No.: US 12,564,614 B2
(45) Date of Patent: Mar. 3, 2026

(54) PHARMACEUTICAL COMPOSITION BASED ON PLANT EXTRACTS FOR THE TREATMENT OF FIBROMYALGIA, RHEUMATOID ARTHRITIS, LUPUS AND OTHER AUTOIMMUNE DISEASES

(71) Applicant: Rosa Maria Portillo Rosado, Santo Domingo (DO)

(72) Inventor: Rosa Maria Portillo Rosado, Santo Domingo (DO)

( * ) Notice: Subject to any disclaimer, the term of this patent is extended or adjusted under 35 U.S.C. 154(b) by 753 days.

(21) Appl. No.: 17/754,945

(22) PCT Filed: Jun. 18, 2020

(86) PCT No.: PCT/DO2020/050002
§ 371 (c)(1),
(2) Date: Mar. 13, 2023

(87) PCT Pub. No.: WO2021/078349
PCT Pub. Date: Apr. 29, 2021

(65) Prior Publication Data
US 2023/0285487 A1    Sep. 14, 2023

(30) Foreign Application Priority Data

Oct. 23, 2019    (DM) ................................. P2019-0272

(51) Int. Cl.
| | |
|---|---|
| A61K 36/288 | (2006.01) |
| A61K 9/19 | (2006.01) |
| A61K 36/42 | (2006.01) |
| A61K 36/484 | (2006.01) |
| A61K 36/54 | (2006.01) |
| A61K 36/81 | (2006.01) |
| A61K 36/8945 | (2006.01) |
| A61P 19/02 | (2006.01) |
| A61P 29/00 | (2006.01) |
| A61P 37/06 | (2006.01) |

(52) U.S. Cl.
CPC .............. *A61K 36/288* (2013.01); *A61K 9/19* (2013.01); *A61K 36/42* (2013.01); *A61K 36/484* (2013.01); *A61K 36/54* (2013.01); *A61K 36/81* (2013.01); *A61K 36/8945* (2013.01); *A61P 19/02* (2018.01); *A61P 29/00* (2018.01); *A61P 37/06* (2018.01)

(58) Field of Classification Search
CPC ........ A61K 36/288; A61K 9/19; A61K 36/42; A61K 36/484; A61K 36/54; A61K 36/81; A61K 36/8945; A61P 19/02; A61P 29/00; A61P 37/06
See application file for complete search history.

(56) References Cited

U.S. PATENT DOCUMENTS

| | | | |
|---|---|---|---|
| 6,541,045 | B1 | 4/2003 | Charters |
| 2003/0131425 | A1 | 7/2003 | Hoeffkes |
| 2007/0041925 | A1 | 2/2007 | Picano |
| 2015/0182441 | A1 | 7/2015 | Goutsis |
| 2015/0209261 | A1 | 7/2015 | Ross |
| 2018/0344796 | A1 | 12/2018 | Hursky |

FOREIGN PATENT DOCUMENTS

| | | | |
|---|---|---|---|
| BR | 102014029858 | | 10/2016 |
| CA | 3067899 | | 1/2019 |
| CN | 101675967 | | 3/2010 |
| CN | 103585589 | | 2/2014 |
| CN | 104146267 | | 11/2014 |
| CN | 104996991 | | 10/2015 |
| CN | 107951803 | | 4/2018 |
| CN | 110090284 | | 8/2019 |
| EP | 1779838 | | 5/2007 |
| ES | 2395418 | | 2/2013 |
| ES | 2581180 | | 9/2016 |
| ID | P202407457 A | * | 9/2024 |
| JP | 2013053171 | | 3/2013 |
| KR | 101509608 | | 4/2015 |
| WO | WO8808711 | | 11/1988 |

OTHER PUBLICATIONS

Doi T, et al, ID-P202407457-A, machine translation, 46 pages. (Year: 2024).*
Bahare Salehi et al: "Dioscorea Plants: A Genus Rich in Vital Nutra-pharmaceuticals—A Review", Iranian journal of pharmaceutical research: IJPR, Jan. 1, 2019 (Jan. 1, 2019), pp. 68-89, XP055753882, Tehran, Iran, DOI: 10.22037/ijpr.2019.112501. 13795 Retrieved from the Internet: URL:https://www.ncbi.nlm.nih.gov/pmc/articles/PMC7393038/pdf/ijpr-18-068.pdf.
Gallo L et al.: "A comparative study of spray-dried medicinal plant aqueous extracts. Drying performance and product quality", Chemical Engineering Research and Design, vol. 104, 2015, pp. 681-694, XP029357463, Retrieved from the Internet [retrieved on Mar. 4, 2021], DOI: dx. doi.org/10.1016/j.cherd. 2015.10.00 9.

(Continued)

*Primary Examiner* — Aaron J Kosar
(74) *Attorney, Agent, or Firm* — Defillo & Associates, Inc.; Evelyn A. Defillo

(57) ABSTRACT

Compositions and pharmaceutical forms for the treatment of fibromyalgia, rheumatoid arthritis, systemic lupus erythematosus and autoimmune diseases associated with pain and inflammation of the muscles and joints with natural active ingredients in the form of lyophilized powders of aqueous extracts of Dandelion (*Taraxacum officinale*), Watermelon (*Citrullus lanatus*), Mapuey or white yam, (*Dioscorea trifid*), Licorice (*Glycyrrhiza glabra*), tomato (*Solanum lycopersicum*) and bay leaves (*Laurus nobilis*), as well as procedures for obtaining and preparing associated with the development of the different compositions and pharmaceutical forms.

6 Claims, No Drawings

(56)     References Cited

OTHER PUBLICATIONS

Eroglue et al.: "Optimization of aqueous extraction and spray drying
conditions for efficient processing of hibiscus blended rosehip tea
powder", J. Food Process. Preserv., vol. el3643, 2018, pp. 1-9,
XP055813860, DOI: 10.1111/jfpp.13643.

* cited by examiner

PHARMACEUTICAL COMPOSITION BASED ON PLANT EXTRACTS FOR THE TREATMENT OF FIBROMYALGIA, RHEUMATOID ARTHRITIS, LUPUS AND OTHER AUTOIMMUNE DISEASES

CROSS REFERENCE TO RELATED APPLICATION

This application is a national stage entry of PCT/DO2020/050002 filed Jun. 18, 2020, under the International Convention and claiming priority over Dominican Republic Patent Application No. P20190272 filed Oct. 23, 2019.

FIELD OF INVENTION

The present invention refers to pharmaceutical compositions for the treatment of fibromyalgia, rheumatoid arthritis, systemic lupus erythematosus and diseases autoimmune disorders associated with pain and inflammation of the muscles and joints, more particularly to a pharmaceutical formulation obtained from natural plant extracts for the treatment of fibromyalgia and autoimmune diseases associated with pain and inflammation of the muscles and the joints as well as the method of obtaining said composition.

BACKGROUND

Autoimmune diseases are disorders in which the immune system attacks the body, they are very complex diseases and their causes are multiple, they can be associated with environmental and genetic conditions. They are presented in about 5% of the population and if they are not detected and treated in time, they can seriously compromise the health of those who suffer from them, with loss of quality of life and high costs for health services. The diseases Autoimmune diseases are part of a group known as non-chronic diseases, communicable and the most common are rheumatoid arthritis and lupus erythematosus systemic, where one of its most common and important episodes is pain associated with inflammatory processes of muscles and joints. For its part, fibromyalgia is one of the most common rheumatological diseases. frequent with manifestations of pain; of unknown cause and difficult to diagnose. There is some evidence about this disease mechanisms that can lead to fibromyalgia, the data suggest that the symptoms of the disease are probably caused by a central alteration, at the cerebral level, of sensitivity to pain, rather than by a dysfunction in the peripheral tissues of the body. These mismatches make the patient experiences great pain in the tissues, with no apparent damage in them. It is also recognized that psychological factors have a great influence on the symptoms of fibromyalgia and associated problems, although they are not considered within the common mental disorders.

Recent research has found a close relationship between predisposition to this disease as a result of factors such as an accident, a trauma, surgery, exposure to toxic substances or viral infections, also with altered levels of certain substances in the body as serotonin, tryptophan, substance P, glutamic acid, which They intervene in neurochemical processes, producing greater susceptibility to pain. Researchers have also recognized that they may be factors triggers of fibromyalgia chronic infections, viral infections, inflammatory processes, or muscle diseases. It has recently been discovered a retrovirus, XMRV, which could be involved in the appearance of the fibromyalgia.

More recent studies have shown that patients with fibromyalgia have alterations in the nociceptive system, that is, in the structures of the nervous systems that regulate the perception and response to pain, this system also aims to detect any possible threat or damage that occurs in the body, in its normal functioning and in its relationship with the environment. Therefore, this system is responsible for the detection and analysis of all those potentially noxious stimuli. Another recent finding is that 70% of nerve fibers of type C, responsible for conducting the painful stimulus from Peripheral tissues up to the spinal cord are injured in most these patients with fibromyalgia, concluding that this factor could be considered key to explaining pain and other sensory symptoms, as well as mechanisms of induction and maintenance of the disease.

To date there is no specific drug, effectively recognized for the treatment of this ailment, only treatments with analgesics or classic anti-inflammatoirer pain modulating drugs are incorporated; antidepressants and anticonvulsants are also applied mainly, with the goal of improving sleep, fatigue, depression, muscle spasms, and pain presented to the patient. In this regard, for example, the FDA has proposed for the treatment of this condition, Pregablin, used for the treatment of neuropathy, which has been shown to reduce pain and improve function in people with fibromyalgia. The substance Duloxetine, another antidepressant that is commonly used to treat fibromyalgia.

More recently and since the decriminalization of its use and consumption for therapeutic, the application of medical *cannabis* is strongly valued to combat chronic pain in different types of ailments, including fibromyalgia Some statistics report that between 30 and 40% of people with fibromyalgia should stop working and this is a worrying factor from the point of view of point of view of health and even more so when it is estimated that most of the People with fibromyalgia will be hospitalized at least once every 3 years, which indicating that it is a serious problem for public health systems. According to statistics, for example 3.7 million Americans, approximately 1 of every 73 people have fibromyalgia. Of these people, between 80 and 90%, approximately 1 in 50 people are women according to statistics published in 2018 by the American College of Rheumatology, this makes it the second most common ailment of the musculoskeletal system where osteoarthritis ranks first. It is recognized that women of childbearing age are mainly affected by fibromyalgia. In fact, it is claimed that between 80 to 90% of those diagnosed with fibromyalgia are women. It is recognized that most of these women have a family member with fibromyalgia, so such as other rheumatic conditions, such as rheumatoid arthritis, lupus systemic erythematosus, ankylosing spondylitis.

Some boys and men are also known to be affected with this ailment, even in the case of children are often diagnosed mistakenly despite having growing pains or problems with behavior and ineffective treatments are applied. The symptoms of fibromyalgia are often difficult to diagnose because they are like symptoms of other disorders, such as chronic fatigue. other reasons for misdiagnosis is based on the fact that there is currently no tests for fibromyalgia, although research is being carried out for this; to Fibromyalgia is often not accepted as a legitimate disorder by some doctors and in others the symptoms confuse it with depression. The most common symptoms identified in patients with fibromyalgia disable them occupationally, for example according to statistics from the American College of Rheumatology are the following:

90% of people have sensitivity in the jaw or face.

50% of people are sensitive to smells, noise, bright lights, medicines and various foods.

50% of people with fibromyalgia also suffer from headaches or migraines.

83% of people with fibromyalgia suffer from emotional distress.

80% of people with fibromyalgia do not handle changes well climatic.

79% of people with fibromyalgia have trouble sleeping.

70% of people with fibromyalgia cannot perform an activity strenuous.

50% of people with fibromyalgia are physically inactive.

People with fibromyalgia are 3.4 times more likely to have of major depression.

So far, no drug has been shown to be effective enough to treat fibromyalgia. The drugs anti-inflammatoirech as non-steroidal anti-inflammatory drugs (NSAIDs), are not effective for fibromyalgia in most cases and are generally at high risk of gastrolesivity, and antidepressant medications are often prescribed, but they also have side effects. Some popular home remedies from natural plants are recognized for relieve some symptoms, including Dandelion, which is said to help strengthen the connective tissue and reduce pain and for this it is recommended to take it in infusion twice a day for four to six weeks. They also suggest the blueberry and radish smoothie for its antioxidant properties for patients with fibromyalgia. Turmeric is also recommended for having properties medicinal and antiseptic and it is suggested to consume powder mixed with milk or water to calm muscle pain and help in the treatment of fibromyalgia.

Ginger is also known to improve joint mobility and has anti-inflammatory and analgesic properties, so its consumption is recommended I stop patients with fibromyalgia, for which they suggest consuming dissolved powder in water and drink this solution twice a day.

The plant called horsetail is also recommended, which has properties analgesics, so it is a remedy for pain and is recognized as a good infusion to treat fibromyalgia, starting from a decoction for 30 minutes of 100 grams of horsetail for every liter of water and take one or two glasses a day.

Other treatment alternatives are known in the patent literature for fibromyalgia from medicinal plant extracts, including the patent US2018344796 from the title Method for treating fibromyalgia published in 2018, where HURSKY MARGERY teaches a treatment to alleviate the symptoms of fibromyalgia by daily administration of a regimen comprising a combination of natural ingredients selected from a group consisting of turmeric extract, boswellia extract, dandelion root, grape seed, green tea, a complex of bioflavonoids, acetyl L-carnitine and vitamin B12. Such ingredients are generally safe for human consumption. This patent refers that like the other ingredients, dandelion is a herb that has been used as a salad green and in soups, wines, and teas for many years. Dandelion root contains chemicals that decrease swelling and inflammation. As such, the daily regimen of the present the invention may include the administration of 1500 mg of ground dandelion root.

In patent WO8808711 under the title Pharmaceutical substance, published in 1988, BADMAJEW VLADIMIR shows a pharmaceutical composition composed exclusively by vegetable components that is suitable for the treatment of abdominal pain in particular in women, for example, of the syndrome premenstrual This pharmaceutical substance is composed of the following substances dehydrated and compressed in powder form: *Trichosanthes palmata* (radix), of the Cucurbitaceae family; *Polygonum avicular* (herb), of the Polygonaceae family; *Tribulus terrestris* (radix), from the Zygophylae family, *Taraxacum officinale* (radix), from the Compositae family.

In patent ES2395418 entitled: "Compositions for herbal teas, enriched with dried herbal extracts", published in 2005, MERCATI VALENTINO teaches compositions for herbal teas, which have a wide stability capacity for storage; This composition includes at least one plant material for conventional herbal teas, and one of the following mixtures of dry extracts, obtained by lyophilization techniques and in form of a water-dispensable granule as dry extract of cohosh root black in a percentage of 50%+dry extract of passion flower in a percentage 50%; dry extract of broom roots in a percentage of 21.8%+extract dry red vine leaves in a percentage of 31.3%+mint powder in a percentage of 46.9%; dry extract of dandelion roots in a percentage of 68%+dry extract of milk thistle seeds in a percentage of 10%+dry extract of java tea leaves in a percentage of 22%; dry extract of 80% chamomile flowers+powdered lemon balm leaves in a percentage of 20%.

DESCRIPTION OF THE INVENTION

The present invention aims to develop formulations from natural extracts from different plants as active ingredients for the treatment of fibromyalgia, rheumatoid arthritis, systemic lupus erythematosus and autoimmune diseases associated with pain and inflammation of the muscles and the joints. More particularly, the present invention has as its object the formulation of different pharmaceutical forms such as capsules, tea, drinkable ampoules and ampoules of injectable solution, comprising Dandelion powder extracts (*Taraxacum officinale*), Watermelon (*Citrullus lanatus*), Mapuey or white yam, (*Dioscorea trifid*), licorice (*Glycyrrhiza glabra*), tomato (*Solanum lycopersicum*) and bay leaves (*Laurus nobilis*), together with preservatives for treatment of patients suffering from fibromyalgia and autoimmune diseases such as rheumatoid arthritis and systemic lupus erythematosus associated with pain and inflammation of the muscles and joints, surprisingly obtaining a remarkable improvement of the patients affected with these diseases, in treatment periods ranging from 1 to 7 days; after applying the regimen of administration; It has been found that the improvement process is integral and significant in the symptomatology of the patient affected with fibromyalgia and autoimmune diseases.

DETAILED DESCRIPTION OF THE INVENTION

The qualitative and quantitative composition by weight of the active ingredients, solvents and preservatives that are proposed in this formulation as well as their function within the composition is as follows:

| | | |
|---|---|---|
| Freeze-dried extract of Dandelion | 10%-50% | Active Ingredient |
| Watermelon Extract | 10%-30% | Active Ingredient |
| Mapuey Extract | 4%-15% | Active Ingredient |
| Liquorice Extract | 4%-7% | Active Ingredient |
| Tomato Extract | 1%-3% | Active Ingredient |
| Laurel Extract | 1%-5% | Active Ingredient |
| Sodium Benzoate Extract | 0.25% | Perseverant |
| Potassium Sorbate Extract | 0.25% | Perseverant |
| Treated Water (optionally) | 15%-19.5% | Solvent |

Procedure for Making Capsules:

The procedure developed for the manufacture of capsules consists of several stages that first go through a classification and selection phase, then proceed to mix with heat between 3° and 40° C., then lead to aqueous extraction of the active ingredients at temperatures of 90 to 96° C. with stirring every five minutes, later this extract is filtered and add the preservatives salts and proceed immediately to the spraying by dried in a Spray Dryer ADL 311, then the powder thus obtained is taken to the encapsulation process in hard gelatin capsules.

The procedure for preparing these capsules includes several stages:

1. In the first stage of the process, the different raw materials are prepared, which entails the inspection, classification, and approval of the raw material to be used in the production of the final product, which will reach a final product in powder form which is introduced into hard gelatin capsules.

2. After the raw materials have been approved in the receiving area of raw materials, they go to the pre-production area where they are prepared for entry into the production area, it is in this area where they are removed the shell to those raw materials that require it, as well as the seeds, they are cleaned and rinsed with treated water coming from the plant of treatment.

3. As the raw materials leave this area, they enter the production area where enter a stainless-steel mixer with temperature control, which is fed with steam from a pyro-tubular boiler, which allows achieving the temperature rise in it. In this mixer we add all the raw materials of the formula minus the preservatives, because these must be be added in the final stage of the process at a temperature of 30° C. to 40° C. to prevent its degradation by temperature and then damage the product through weather.

In this mixer the different raw materials all mixed inside the same, they are subjected to a temperature of 96° C. (205° F.), followed by periods of agitation every 5 minutes, this with the aim that at that temperature the water can absorb the properties and nutrients of each of the raw materials present in the mixer, this will allow us to obtain a well charged liquid, rich of all the properties from the herbs, fruits and raw materials that were subjected in this part of the production process.

4. The resulting liquid that comes out of the mixer now goes to another piece of equipment called pressure filter, it is in this equipment where even the smallest particle is separated solid that may be mixed with the liquid extract, the objective in this part of the process is to obtain a liquid free of solid particles. In this stage We will take the opportunity to add the Preservatives.

5. The already filtered liquid is passed to a pulverizing equipment or dryer by spraying of the Spray Dryer ADL 311 type, at this stage of the process what is achieve is that the liquid from the pressure filter turns into dust. The feed of the concentrated and filtered liquid is fed by means of a pump peristaltic with silicone hose, this spray equipment has a temperature system, spray system at the tip of the nozzle outlet, blower, heater, suction filter and exhaust filter, through the which performs the drying and subsequent spraying of the liquid, managing to convert it into dust.

6. Dust obtained from Spray equipment now passes through to a Machine Encapsulator NJP 1200D, which is an automatic machine that allows encapsulate the powder product in Gelatin Capsules, which can be Capsules of #0 Gelatin, for example in Red/Black #0 hard gelatin capsules, from the company ACG Associated Capsules Pvt Ltd.

7. Once the product is encapsulated, these capsules are now going to pass through a piece of equipment called SP-G100 Capsule Packing Machine, the goal to be achieved in this equipment is to place the capsules in the final packaging, which will serve as vehicle to deliver the product to the final consumer.

The capsules thus obtained according to the process described have a stability 2-year storage environment.

Example 1

With the capsules obtained according to example 1, they were subjected to treatment of patients diagnosed with fibromyalgia, rheumatoid arthritis and lupus erythematosus systemic and autoimmune diseases associated with pain and inflammation of muscles and joints for a period of one month with a dosage of two capsules a day with a composition of ingredients of:

| Lion Teeth | 40% |
| --- | --- |
| Watermelon | 27.5% |
| Mapuey | 15% |
| Licorice | 7% |
| Tomato | 5% |
| Bay | 5% |
| Sodium Benzoate | 0.25% |
| Potassium sorbate | 0.25% |

Procedure for Making Tea Bags:

The homogeneous powder obtained according to steps 1 to 5 described in the procedure for obtaining the capsules is now packed in bags or sacks of porous paper, silk or nylon, similar to those used in tea bags or similar from which an infusion is prepared with hot water useful in the treatment of fibromyalgia and autoimmune diseases.

The bags thus obtained according to the described process have an ambient stability 2-year storage.

Example 2

Patients diagnosed with fibromyalgia, arthritis rheumatoid and systemic lupus erythematosus and associated autoimmune diseases with pain and swelling of the muscles and joints for a period of a month with a dosage of four to six cups of tea per day, with a composition of ingredients per bag:

| Lion Teeth | 50% |
| --- | --- |
| Watermelon | 29.5% |
| Mapuey | 8% |
| Licorice | 7% |
| Tomato | 3% |
| Bay | 2% |
| Sodium Benzoate | 0.25% |
| Potassium sorbate | 0.25% |

Procedure for the Preparation of a Bag of Drinkable Ampoules:

The procedure for the preparation of drinkable ampoules consists of the following Steps:

1. In the first stage of the process, the different raw materials are received in the plant, which will go through a process of inspection, classification, and approval to be used in the production of our final product, which will be ampoules drinkable.

2. After the raw materials have been approved in the receiving area of raw materials, they go to the pre-production area where they are prepared for entry into the production area, it is in this area where they are removed the shell to those raw materials that require it, as well as the seeds, they are cleaned and rinsed with treated water coming from the plant of treatment.

3. As the raw materials leave this area, they enter the production area where the first piece of equipment or unit operation they enter is a steel mixer stainless steel with temperature control, which is fed with steam, which allows to achieve the temperature increase in it. in this mixer we add all the raw materials of our formula except the Preservatives, because these must be added at a temperature of 30° C. to 40° C. to avoid its degradation due to high temperatures and that later the product cannot be supplied expected effect on the final product.

4. In this mixer the different raw materials all mixed inside the same, they are subjected to a temperature of 96° C. (205° F.), followed by periods of agitation every 5 minutes, this with the aim that at that temperature the water can absorb the properties and nutrients of each of the raw materials present in the mixer, this will allow us to obtain a well charged liquid, rich of all the properties from the herbs, fruits and raw materials that were subjected in this part of our production process.

5. The resulting solution that comes out of the mixer now goes to another piece of equipment called pressure filter, it is in this equipment that even the smallest particle is separated solid that can be mixed with our solution, the objective in this part of the process is to obtain a solution free of solid particles. In this stage we will take the opportunity to add those pending products that we did not add in the previous stage due to high temperatures, these are Sodium Benzoate and Potassium Sorbate.

6. The container chosen to store the final product is the container: Ampoules Specials For Drinkable Solutions.

7. These containers are subjected to an automatic washing process in a machine that provides pressurized water jet, this water is totally purified.

8. Once these containers leave the washing process, they enter a machine sterilization or dryer that will be responsible for sterilizing and drying the containers by the action of high temperatures.

9. Upon leaving the sterilization machine or dryer, these containers enter a SCT Pharma oven, where the depyrogenation process will be carried out, which is nothing more than that process that will allow us the total or almost total reduction of bacterial endotoxins (pyrogens), in other words what we are looking for is to obtain ampoules free of all microorganisms and undesirable pathogenic substances, this we achieve this through processes that use high temperatures, such as those that have been previously exposed.

10. The resulting solution obtained in step 5, coming from the filter, will now pass to a piece of equipment called the Vial Filling and Sealing Machine, the objective in this step is to dose the filtered solution as quickly as possible into the ampoule's drinkable, always taking care not to wet the neck of the blisters. This machine is will later be in charge of sealing the valves, since it has a system of sealing for this type of blisters.

11. The next stage is the stage called labeling, stage in which the label is placed label to the product including elementary information such as: Number of Lot, Dosage, Manufacture Date, Expiration Date, etc.

12. In the final stage of our process, we find ourselves storing our finished product, under favorable conditions of temperature and humidity, characteristic of this type of product. The drinkable ampoules thus obtained according to the process described have a stability 2-year storage environment.

Example 3

Patients diagnosed with fibromyalgia, arthritis rheumatoid, systemic lupus erythematosus and associated autoimmune diseases with pain and swelling of the muscles and joints, for a period of a month with a dosage of four to six drinkable ampoules per day, with a composition of ingredients per ampoule of:

| | |
|---|---|
| Properly Treated Water | 19.5% |
| Dandelion lyophilized extract | 30% |
| Watermelon extract | 30% |
| Mapue extract | 8% |
| Licorice Extract | 7% |
| Tomato Extract | 3% |
| Laurel extract | 2% |
| Sodium Benzoate | 0.25% |
| Potassium sorbate | 0.25% |

Procedure for the Preparation of an Intramuscular Injectable Solution.

The procedure for the preparation of an intramuscular injectable solution, consists of the following steps:

1. In the first stage of the process we receive the different raw materials in the plant, which will go through a process of inspection, classification, and approval to be used in the production of our final product, which will be a intramuscular injectable solution.

2. After the raw materials have been approved in the receiving area of raw materials, they go to the pre-production area where they are prepared for entry into the production area, it is in this area where they are removed the shell to those raw materials that require it, as well as the seeds, they are cleaned and rinsed with treated water coming from the plant of treatment.

3. As the raw materials leave this area, they enter the production area where the first piece of equipment or unit operation they enter is a steel mixer stainless steel with temperature control, which is fed with steam, which allows to achieve the temperature increase in it. in this mixer we add all the raw materials of our formula except the Preservative, the Lidocaine and Ascorbic Acid, because these must be added to a temperature from 30° C. to 40° C. to avoid its degradation due to high temperatures and that later they cannot have the expected effect in the final product.

4. In this mixer the different raw materials all mixed inside the same, they are subjected to a temperature of 96° C. (205° F.), followed by periods of agitation every 5 minutes, this with the aim that at that temperature the water can absorb the properties and nutrients of each of the raw materials present in the mixer, this will allow us to obtain a well charged liquid, rich of all the properties from the herbs, fruits and raw materials that were subjected in this part of our production process.

6. The resulting solution that comes out of the mixer now goes to another piece of equipment called pressure filter, it is in this equipment where we are going to separate even the smallest solid particle that can be mixed with our solution, the objective in this part of the process is to obtain a solution free of solid particles. In this stage we will take the opportunity to add those pending products that we did not add in the previous stage due to the high temperatures, these are the Preservative, the Lidocaine and Ascorbic Acid.

7. The container chosen to store the final product is the container: Ampoule of Glass for injectable solutions.

8. Once these containers leave the washing process, they enter until a sterilization machine or dryer that will oversee sterilizing and drying the containers through the action of high temperatures.

9. Upon leaving the sterilization machine or dryer, these containers enter a SCT Pharma oven, where the depyrogenation process will be carried out, which is nothing more than that process that will allow us the total or almost total reduction of bacterial endotoxins (pyrogens), in other words what we are looking for is to obtain ampoules free of all microorganisms and undesirable pathogenic substances, this we achieve this through processes that use high temperatures, such as those that have been previously exposed.

10. The resulting solution we got in step 5, coming from the filter, is now will go to a piece of equipment called the Vial Filling and Sealing Machine, the goal in this step is to dose the filtered solution as quickly as possible into the glass ampoules, always taking care not to wet the neck of the ampoules. This stage will end with the injection of inert gas. This machine will handle after sealing the valves, since it has a sealing system to glass-type ampoules, which were the types of packaging chosen in our process.

11. Once we have the glass ampoules ready, containing the product inside and properly sealed, they are sterilized, this with the aim of eliminating all possible microorganism or contamination that has remained on the outside of the container during the process, for which sterilization equipment is used called autoclave, the process that is carried out in this equipment is Sterilization By Moist Heat, in which this equipment uses saturated water vapor, at a pressure of 15 pounds which allows the chamber to reach a temperature of 121° C., in this equipment the ampoules will last around 15 minutes crossing the sterilization process.

12. The next stage is the stage called Labeling, stage in which the label is placed label to the product including elementary information such as: Number of batch, dose, route of administration, manufacturing date, expiration date, etc.

The ampoules of injectable solution thus obtained according to the described process have ambient storage stability of 2 years.

Example 4

Patients diagnosed with fibromyalgia, arthritis rheumatoid, systemic lupus erythematosus and associated autoimmune diseases with pain and swelling of the muscles and joints for a period of one month with a dosage of two to four ampoules of solution for injection intramuscular daily, with a composition of ingredients per ampoule of:

| | | |
|---|---|---|
| Properly Treated Water | 18.01% | |
| Dandelion lyophilized extract | 30% | |
| Watermelon extract | 30% | |
| Mapue extract | 8% | |
| Licorice Extract | 7% | |
| Tomato Extract | 3% | |
| Laurel extract | 2% | |
| Lidocaine | 1.8% | Anesthetic |
| Sodium Benzoate | 0.17% | Intramuscular Preservative |
| Ascorbic Acid 0.02% | 0.02% | Antioxidant |

At the end of the treatment period, a high efficacy of these pharmaceuticals' forms was demonstrated—capsules, tea, drinkable ampoules and ampoules of injectable solution—in improving the comprehensive picture of patients diagnosed with fibromyalgia, arthritis rheumatoid, systemic lupus erythematosus and associated autoimmune diseases with pain and inflammation of muscles and joints headaches and muscular, as well as insomnia and depressive states.

During the tests, a group of 20 patients were taken and evaluated through of a self-assessment of your condition before starting the plan and after 30 days of treatment, for this assessment they were asked to rate their improvement from 1 to 5 Regarding their situation at the start of treatment, the parameters to be assessed were headaches, muscle aches, joint pains, insomnia and depression. The following table shows the results of the self-assessment of their improvement with treatment.

Table No. 1 Tabulation of the self-assessment of a sample of 20 patients in the improvement of his individual state of fibromyalgia in this case, with the treatment by a month with the capsules object of the present invention, evaluation of the improvement with a weighting from 1 to 5

TABLE NO. 1

Tabulation of the self-assessment of a sample of 20 patients in the improvement of his individual state of fibromyalgia in this case, with the treatment by a month with the capsules object of the present invention, evaluation of the improvement with a weighting from 1 to 5

| Patient | Headaches | | Muscular and joints pains | | Insomnia | | Depressive states | |
|---|---|---|---|---|---|---|---|---|
| | Before | Assessment | Before | Assessment | Before | Assessment | Before | Assessment |
| 1 | Yes | 4 | Yes | 5 | Yes | 5 | Yes | 4 |
| 2 | No | 0 | Yes | 5 | Yes | 5 | Yes | 4 |
| 3 | Yes | 4 | Yes | 5 | No | 0 | Yes | 4 |
| 4 | Yes | 5 | Yes | 5 | No | 0 | Yes | 4 |
| 5 | Yes | 3 | Yes | 3 | No | 0 | Yes | 5 |
| 6 | Yes | 2 | Yes | 4 | Yes | 5 | Yes | 5 |

TABLE NO. 1-continued

Tabulation of the self-assessment of a sample of 20 patients in the
improvement of his individual state of fibromyalgia in this case, with the treatment by a
month with the capsules object of the present invention, evaluation of the improvement
with a weighting from 1 to 5

|  | Headaches | | Muscular and joints pains | | Insomnia | | Depressive states | |
|---|---|---|---|---|---|---|---|---|
| Patient | Before | Assessment | Before | Assessment | Before | Assessment | Before | Assessment |
| 7 | Yes | 5 | Yes | 4 | Yes | 5 | Yes | 5 |
| 8 | Yes | 5 | Yes | 4 | Yes | 5 | Yes | 5 |
| 9 | Yes | 5 | Yes | 5 | Yes | 4 | Yes | 3 |
| 10 | Yes | 4 | Yes | 5 | Yes | 4 | Yes | 4 |
| 11 | No | 0 | Yes | 5 | Yes | 4 | Yes | 4 |
| 12 | Yes | 4 | Yes | 5 | Yes | 4 | Yes | 4 |
| 13 | No | 0 | Yes | 3 | Yes | 4 | Yes | 5 |
| 14 | Yes | 4 | Yes | 3 | No | 0 | Yes | 5 |
| 15 | Yes | 3 | Yes | 4 | Yes | 4 | Yes | 5 |
| 16 | Yes | 3 | Yes | 4 | Yes | 4 | No | 0 |
| 17 | Yes | 4 | Yes | 4 | No | 0 | No | 0 |
| 18 | Yes | 3 | Yes | 4 | Yes | 5 | Yes | 5 |
| 19 | Yes | 5 | Yes | 4 | Yes | 5 | Yes | 5 |
| 20 | Yes | 5 | Yes | 4 | Yes | 5 | Yes | 5 |
| Rating average Or the improvement | | 4 | | 4.25 | | 4.53 | | 4.5 |

The results obtained from the self-assessment of each patient who underwent the treatment in the fundamental aspects in which it is manifested diseases such as fibromyalgia, rheumatoid arthritis, systemic lupus erythematosus and autoimmune diseases associated with pain and inflammation of the muscles and joints in just 30 days of treatment is a sample evident that the mechanism of action of these active ingredients is not only to the aspects of relieving pain like other medications that are currently applied for the treatment of this disease as is the case of NSAIDs and opioid derivatives. In the treatment it is verified that the mechanism of action of the quantitative and qualitative combination of active principles not only acts on the nociceptive system but is also an effective anti-inflammatory. in none of the patients who applied the treatment manifested collateral negative reactions.

The invention claimed is:

1. A pharmaceutical composition for the treatment of fibromyalgia, rheumatoid arthritis, systemic lupus erythematosus and associated autoimmune diseases with pain and inflammation of the muscles and joints, the composition comprising:
   a) a heated mixture including as active ingredients:
   an aqueous extract of freeze-dried dandelion (*Taraxacum officinale*),
   an aqueous extract of watermelon (*Citrullus lanatus*),
   aqueous extract of yam, wherein the yam extract is selected from the group consisting of mapuey or white yam (*Dioscorea trifid*),
   an aqueous extract of licorice (*Glycyrrhiza glabra*),
   aqueous extract of tomato (*Solanum lycopersicum*),
   an aqueous extract of bay leaves (*Laurus nobilis*),
   b) at least one preservatives selected from the group consisting of sodium benzoate and potassium sorbate, and
   c) optionally at least one of lidocaine, benzoic acid, or ascorbic acid,
   wherein the composition is an oral medication in the form of a tea or infusion, an oral medication in the form of capsules, an oral medication in the form of drinkable ampoules, or an intramuscular injectable solution.

2. The composition of claim 1, wherein the composition by percent weight thereof comprises:
   10% to 50% of the aqueous extract of freeze-dried dandelion,
   10% to 30% of the aqueous extract of watermelon,
   5% to 15% of the aqueous extract of yam,
   4% to 7% of the aqueous extract of licorice,
   1% to 3% of the aqueous extract of tomato,
   1% to 5% of the aqueous extract of laurel,
   0.25% of sodium benzoate,
   0.25% of potassium sorbate, and
   optionally 15% to 19.5% of the treated water.

3. The composition of claim 1, wherein the composition by percent weight thereof comprises:
   40% of the aqueous extract of freeze-dried dandelion,
   27.5% of the aqueous extract of watermelon,
   15% of the aqueous extract of yam,
   7% of the aqueous extract of licorice,
   5% of the aqueous extract of tomato,
   5% of the aqueous extract of bay leaves,
   0.25% of sodium benzoate,
   0.25% of potassium sorbate, and
   wherein the composition is the oral medication in the form of capsules.

4. The composition of claim 1, wherein the composition by percent weight thereof comprises:
   40% of the aqueous extract of freeze-dried dandelion,
   39.5% of the aqueous extract of watermelon,
   8% of the aqueous extract of yam,
   7% of the aqueous extract of licorice,
   3% of the aqueous extract of tomato,
   2% of the aqueous extract of bay leaves,
   0.25% of sodium benzoate,
   0.25% of potassium sorbate, and
   wherein the composition is the oral medication in the form of a tea or infusion.

5. The composition of claim 1, wherein the composition by percent weight thereof comprises:

19.5% of the treated water,

30% of the aqueous extract of freeze-dried dandelion,

30% of the aqueous extract of watermelon,

8% of the aqueous extract of yam,

7% of the aqueous extract of licorice,

3% of the aqueous extract of tomato,

2% of the aqueous extract of laurel, 0.25% of sodium benzoate, 0.25% of potassium sorbate, and wherein the composition is the oral medication in the form of drinkable ampoules.

6. The composition of claim 1, wherein the composition by percent weight thereof comprises:

18.01% of the treated water,

30% of the aqueous extract of dandelion,

30% of the aqueous extract of watermelon,

8% of the aqueous extract of yam,

7% of the aqueous extract of licorice,

3% of the aqueous extract of tomato,

2% of the aqueous extract of laurel, 1.8% of lidocaine, 0.17% of benzoic acid, 0.02% of ascorbic acid, and wherein the composition is the intramuscular injectable solution.

* * * * *